US008334972B2

(12) United States Patent
Thien

(10) Patent No.: US 8,334,972 B2
(45) Date of Patent: Dec. 18, 2012

(54) METHOD AND DEVICE FOR DETECTING SOILING

(75) Inventor: Marcus Thien, Singapore (SG)

(73) Assignee: Pepperl & Fuchs GmbH, Mannheim (DE)

( * ) Notice: Subject to any disclaimer, the term of this patent is extended or adjusted under 35 U.S.C. 154(b) by 9 days.

(21) Appl. No.: 12/876,788

(22) Filed: Sep. 7, 2010

(65) Prior Publication Data
US 2011/0085161 A1  Apr. 14, 2011

Related U.S. Application Data

(60) Provisional application No. 61/240,405, filed on Sep. 8, 2009.

(30) Foreign Application Priority Data

Sep. 7, 2009  (DE) .......................... 10 2009 040 216

(51) Int. Cl.
*G01N 21/00*  (2006.01)
(52) U.S. Cl. ..................... 356/237.3; 340/601; 340/602; 340/901; 340/425.5; 356/342; 356/442; 356/448; 356/436
(58) Field of Classification Search .................. 340/601, 340/602, 901, 438, 425.5; 356/237.3, 342, 356/436, 432, 442, 448, 445
See application file for complete search history.

(56) References Cited

U.S. PATENT DOCUMENTS

| 4,859,867 A | * | 8/1989 | Larson et al. ................. 250/349 |
| 4,867,561 A | | 9/1989 | Fujii et al. |
| 4,960,996 A | | 10/1990 | Hochstein |
| 5,801,307 A | * | 9/1998 | Netzer ....................... 73/170.17 |

FOREIGN PATENT DOCUMENTS

EP  1 813 961 A2  8/2007
WO  WO 00/35725 A1  6/2000

* cited by examiner

Primary Examiner — Gregory J Toatley
Assistant Examiner — Iyabo S Alli
(74) Attorney, Agent, or Firm — Muncy, Geissler, Olds & Lowe, PLLC

(57) ABSTRACT

A device for detecting soiling, having a light source, which emits a light beam, and a layer having a first boundary surface and a second boundary surface, whereby the light beam emitted by the light source first impinges on the first boundary surface, and part of a light beam fraction, which is scattered at the second boundary surface, impinges on a receiver and forms a measuring signal, and hereby the first boundary surface is set up to scatter part of the incident light beam, and the part impinging on the receiver of the light beam, scattered at the first boundary surface, forms a reference signal, and the device is set up further to determine a measure for the soiling of the second boundary surface from the comparison of the reference signal and measuring signal.

16 Claims, 2 Drawing Sheets ical effort is needed for a comparative
METHOD AND DEVICE FOR DETECTING SOILING This nonprovisional application claims priority under 35 U.S.C. §119(a) to U.S. provisional application No. 61/240,405, which was filed in the US on Sep. 8, 2009 and to German Patent Application No. DE 10 2009 040 216.0, which was filed in Germany on Sep. 7, 2009, and which are herein incorporated by reference.

The invention relates to a device for detecting soiling according to the preamble of claim 1 and a method for detecting soiling according to the preamble of claim 10.

A device and a method for detecting soiling on front panes are disclosed in European Pat. App. No. EP 1 813 961 A. The device has a transmitting unit and a sensor array formed as a receiving unit. The transmitting unit emits light beams with a structured illuminating pattern, which reflects at a predefined angle and by means of focusing optics impinges on a first predefined place on the sensor array. If dirt is present on the outside of the pane, diffuse scattering occurs, part of the scattered light being imaged by the focusing optics on a second place of the sensor array.

Further, another method for detecting and localizing soiling on a translucent coating, particularly an automobile window, is disclosed in International Pat. App. No. WO 00/35725. According to the disclosed method, the intensity of the distribution of the light beam image reflected at the inner and outer boundary surface is determined by means of a sensor array. Accordingly, the light beam image is compared with a stored reference light beam image for a clean pane, to detect soiling of the inner or outer boundary surface.

A method for detecting soiling on an inner or outer glass pane is disclosed inter alia in U.S. Pat. No. 4,867,561. To this end, a first light beam from a first light source is reflected in part at the inner boundary surface and a second light beam from a second light source at the outer boundary surface. The reflected light beams are transmitted by means of an optical system to a receiver. If the boundary surfaces are soiled, the intensities coming into the receiver decline because of the increased fraction of diffuse scattering.

It is a disadvantage that in each case the reference values or the intensity distribution of the beam image must be stored and compared by a processor with the actual measured values. A high computational effort is needed for a comparative image evaluation to determine soiling. Further, the light sources and/or the receivers degrade or have intensity fluctuations, for example, due to changes in the temperature and/or the applied control voltage. An already stored reference pattern of the beam with its intensity distribution is hereby of little suitability as a reference and has a negative impact on the reliable determination of the degree of soiling. Further, such devices with sensor arrays are very cost-intensive.

Against this background, the first object of the invention is to provide a device for detecting soiling and as a second object a method for detecting soiling, each of which reduce the disadvantages of the prior art.

The first object is achieved by a device for detecting soiling with the features of claim 1, and the second object by a method for detecting soiling with the features of claim 10. Advantageous embodiments of the invention are the subject of dependent claims.

According to the first object of the invention for detecting soiling, a device is provided, having a light source, which emits a light beam, and an opaque layer having a first boundary surface and a second boundary surface, whereby the light beam emitted by the light source first impinges on the first boundary surface, and part of a light beam fraction, which is scattered at the second boundary surface, impinges on a receiver and forms a measuring signal, and hereby the first boundary surface is set up to scatter part of the incident light beam, and the part impinging on the receiver of the light beam, scattered at the first boundary surface, forms a reference signal, and the device is set up further to determine a measure for the soiling of the second boundary surface from the comparison of the reference signal and the measuring signal.

According to the second object of the invention, a method for detecting soiling on an opaque layer is provided, whereby the layer has a first boundary surface and a second boundary surface, with a light source, which emits a light beam, and whereby the light beam is directed first to the first boundary surface, and part of the light scattered at the second boundary surface is directed to a receiver and a measuring signal is produced, whereby the first boundary surface is set up in such a way that part of the incident light beam is scattered, and part of the light scattered at the first boundary surface is directed to the receiver and a reference signal is produced, and a measure for the soiling of the second boundary surface is formed from the comparison of the reference signal and the measuring signal.

An advantage of the device or method of the invention is that soiling can be detected in a simple manner and cost-effectively by means of the simultaneous formation of a reference signal and a measuring signal without laborious and cost-intensive image evaluations. Further, a fluctuation in the light intensity of the light source is reliably suppressed, for example, by a change in the temperature and/or due to aging.

According to a refinement, the surface of the first boundary surface is to be roughened to adjust the preferably diffuse scatter fraction of the light beam impinging on the first boundary surface. To this end, chemical as well as mechanical methods or a combination of both methods can be used, whereby both the fraction of the scattered light and its distribution pattern can be adjusted with the degree of roughness. Instead of or in addition to the treatment of the first surface to adjust the scatter fraction, an opaque film can also be applied to the first boundary surface. Both the type of scattering and the scatter fraction can be adjusted with the film flexibly and cost-effectively.

According to another embodiment, it is advantageous to select the optical axis of the light beam so that in the case of a direct reflection of the light beam at the boundary surfaces, the reflected fraction substantially no longer impinges on the receiver directly. To this end, for example, a perpendicular incidence of the light beam on the first boundary surface is preferred. It is achieved as a result that substantially only the scattered light fractions of the two boundary surfaces are transmitted to the receiver.

According to another refinement, the receiver has a first receiving surface and a second receiving surface. Preferably, the light scattered at the first boundary surface and the light scattered at the second boundary surface are directed substantially to different receiving surfaces. Prior-art imaging devices from geometric optics are used to this end. Many types of photosensitive surfaces, such as, for example, solar cells or photosensitive resistors, can be used as receivers. Soiling is detected by means of the comparison of the two signals of the two receiving surfaces, whereby soiling is detected preferably when the measuring signal is greater than the reference signal. According to another refinement, the receiver for this purpose has a reference signal output, connected to an inverting input of an operational amplifier, and a measuring signal output, connected to a noninverting input of the operational amplifier.

It is advantageous further to provide a voltage divider, which is preferably controllable and with which the magnitude of the reference input signal can be adjusted, between the inverting input and the reference signal output. Virtually any threshold values for detecting soiling can be established in a simple way by the voltage divider in conjunction with the inverting input of the operational amplifier. In the first approximation, the statement applies that the higher the reference voltage present at the inverting input, the more insensitive the detection and vice versa.

In another embodiment, a control device for controlling the light source and the voltage divider is provided, whereby the control device has an output for outputting a signal with which soiling is communicated and/or the extent of soiling is communicated with the magnitude of the signal.

According to a preferred refinement, the comparison of the reference signal with the measuring signal is carried out at time intervals by the control device and the result of the comparison is transmitted wirelessly or hard-wired to a host device. For hard-wired transmission, both a single-wire or multiwire bus system is an option. For wireless transmission, radio interfaces such as, for example, Bluetooth and/or GSM are options.

Tests by the applicant have shown that the device or the method can be used advantageously for detecting soiling on the surfaces of solar collectors and/or solar cells and/or glass panes. According to a first alternative, the device is housed and sealed with an opaque layer, which consists preferably of a transparent plastic, most preferably of glass. Accordingly, the device can be mounted in the vicinity or directly connected to the object to be monitored. According to a second embodiment, the opaque layer is replaced by the layer to be monitored, in which a device, open at least in the direction of the light beam to be emitted, is flange-mounted directly on the layer to be monitored.

According to another embodiment, the operation of the device and/or the control device are supplied with the energy of a solar cell. In particular, in the case of use for monitoring a plurality of solar modules, it is preferred in the event of soiling to provide a suitable signal with the novel detection device by the control device by means of an open collector circuit.

The invention will be described in greater detail below with reference to the drawings. In this regard, similar parts are labeled with the identical designations. In the drawing.

Figure 1:
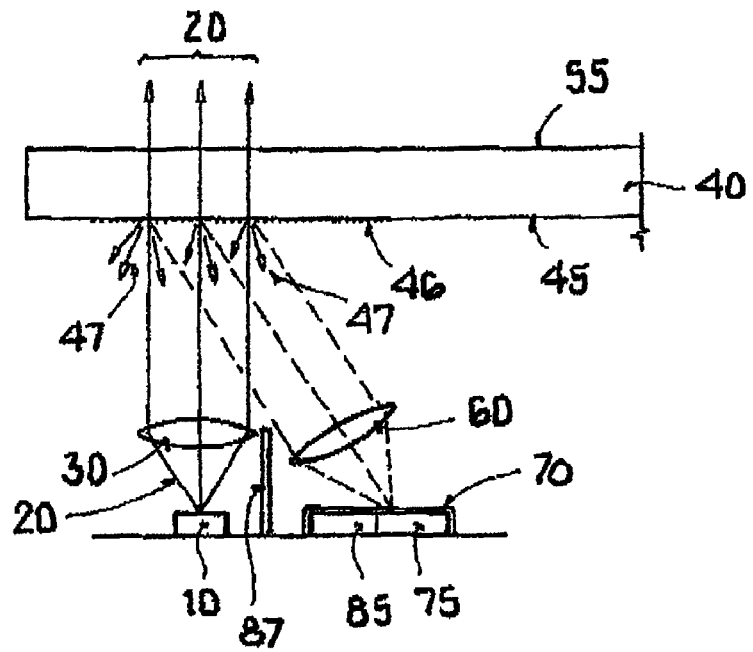
FIG. 1 shows a first embodiment with a clean second boundary surface.

The illustration in FIG. 1 shows a first embodiment of the device of the invention. A light source 10 sends a light beam 20, which is bundled by a lens 30, in the perpendicular direction to a layer 40, which is made preferably of glass and has a first boundary surface 45 and a second boundary surface 55. Boundary surface 45 has a roughness 46 on its surface. The light beam impinges perpendicularly on first boundary surface 40. A diffusely scattered fraction 47 is formed by roughness 46. The remaining light beam 20, due to the perpendicular incidence on second boundary surface 55, now emerges unimpeded from layer 40. Part of the scattered portion 47 is collected by a lens 60 and transmitted substantially to a receiver 70, which has a first reception area 75 and a second reception area 85. Preferably, lens 60 images the scattered fraction 47 on first reception area 75. A screen 87 is provided to shade light source 10 relative to receiver 70.

Figure 2:
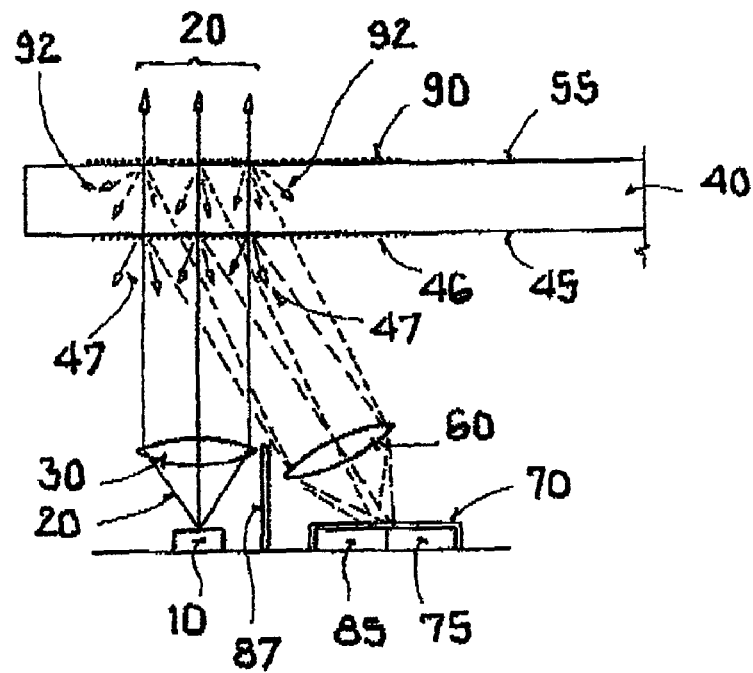
FIG. 2 shows an embodiment according to the illustration in FIG. 1 but with a soiled second boundary surface.

The illustration in FIG. 2 in a refinement shows the device of the invention of FIG. 1 now with soiling 90 on second boundary surface 55 of layer 40. Only the differences from the illustration in FIG. 1 will be explained below. Light beam 20 due to soiling 90 forms a scattered fraction 92, which is scattered at least partially opposite to the direction of incidence of the beam. Part of the scattered fraction 92 is collected by lens 60 and preferably transmitted to second receiving surface 85 of receiver 70.

Figure 3:
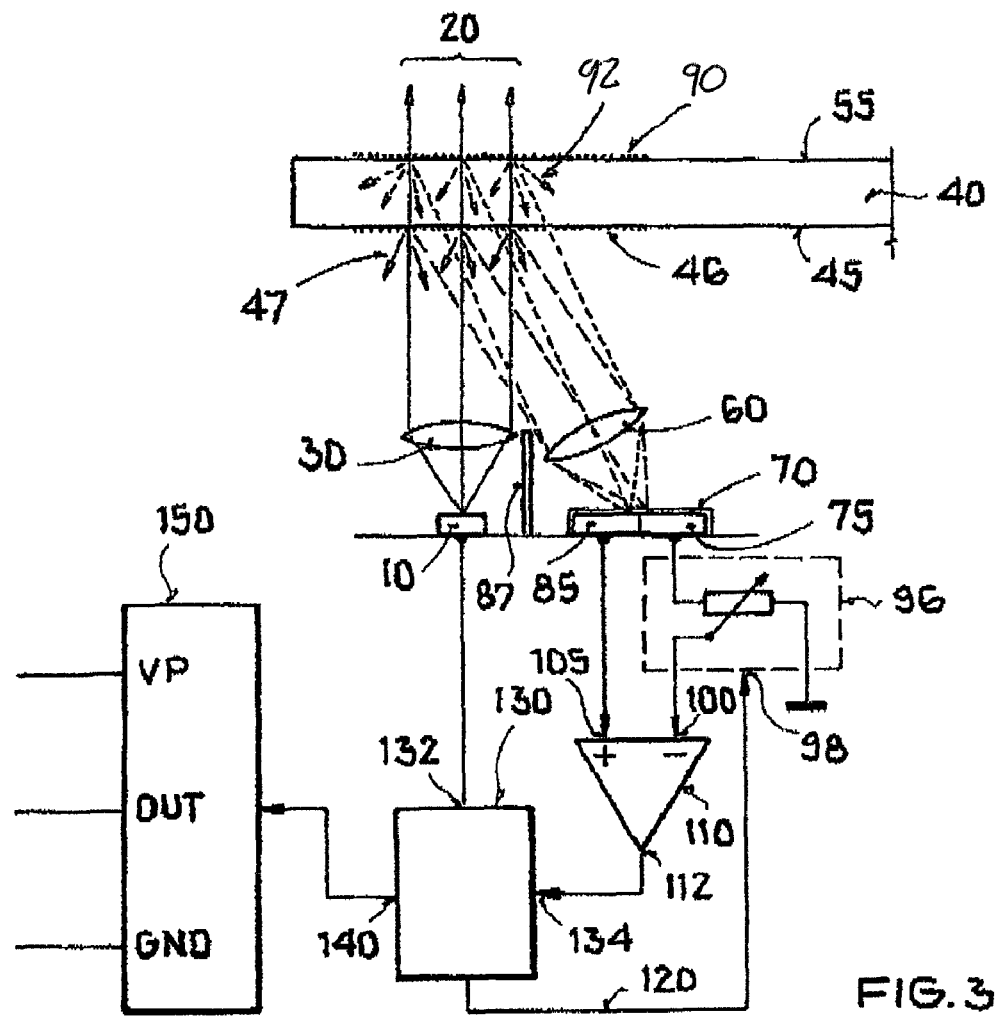
FIG. 3 shows an embodiment according to the illustration in FIG. 2 with a schematic depiction of the evaluation electronics.

In the illustration in FIG. 3, the embodiment is shown with the drawing documents of FIG. 2 connected to evaluation electronics. Only the differences to the explanations provided in relation to FIG. 2 will be set forth below. The first receiving surface 75 is connected to an inverting input 100 of an operational amplifier 110 via a voltage divider 96, which is connected to ground, whereas the second receiving surface 85 is connected to a noninverting input 105 of operational amplifier 110. Voltage divider 96 has a control input 98. Control input 98 is connected to an output 120 of a control device 130. Control device 130 has an output 132, which is connected to light source 10, and an input 134, which is connected to an output 112 of operational amplifier 100. Further, control device 130 has an output 140, which is connected to an interface module 150. Interface module 150 is formed as a three-wire bus with the terminals VP, OUT, and GND.

The principle of operation will now be explained below. If light source 10 is controlled by control device 130, light source 10 emits a bundled light beam 20. Fraction 47, scattered at first boundary surface 45, by means of receiving surface 75 generates a reference signal at inverting input 100 of operational amplifier 110. The magnitude of the reference signal, present at inverting input 100, can be adjusted by control unit 120 by means of controllable voltage divider 96. If no light is scattered at the second boundary surface, the output signal at output 112 of operational amplifier 110 is negative, provided the reference signal is formed as positive. The intensity of the scattered light, impinging on second receiving surface 85, increases with the extent of soiling on second boundary surface 55. As a result, the measuring signal present at noninverting input 105 increases. If the measuring signal now exceeds the reference signal, the output signal at output 112 of operational amplifier 110 becomes positive. The threshold at which a sign change of the output signal at output 112 occurs can be adjusted by means of control device 130 and hereby the sensitivity of the entire device with respect to detection of soiling due to a change of the voltage portion tap of voltage divider 96 over broad ranges.

An advantage of the device is that the fluctuations in intensity are immediately suppressed by the simultaneous determination of the reference signal with the measuring signal from one and the same light source without temporary storage of a reference signal. Further, only the scatter fraction of the light beam is determined without laborious image evaluation and an extremely reliable and cost-effective determination of soiling is made possible by means of a simple electronic comparison of the two analog output signals of the receiving surfaces of the receiver.

Figure 4:
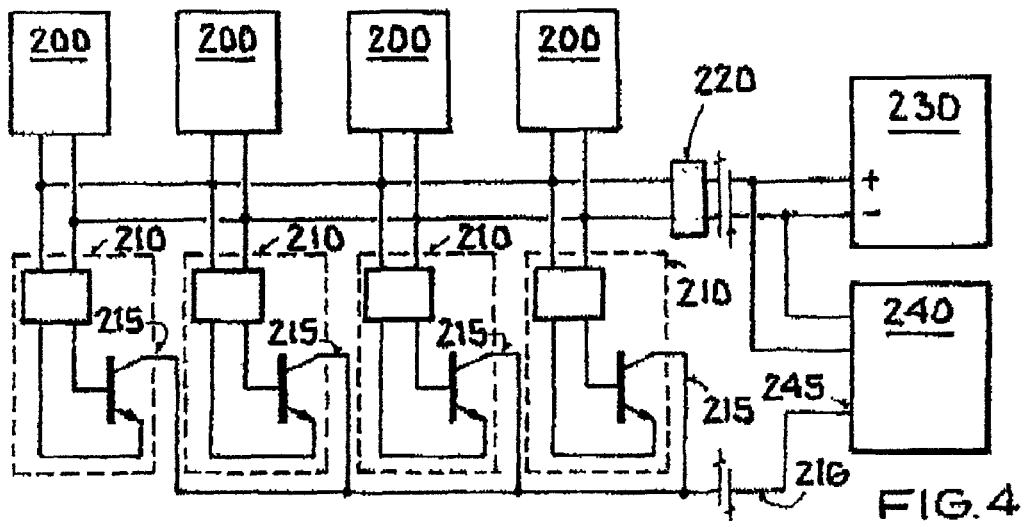
FIG. 4 shows a schematic depiction using the device of the invention in a plurality of solar modules.

The illustration of FIG. 4 shows schematically a use of the device of the invention in a solar system which is made of a plurality of individual modules 200. Each individual module is assigned a detection unit 210 with a device of the invention.

Modules 200 are connected to a line pair 220 to carry off the generated energy with an inverter 230 and a control device 240. The individual detection units 210 are connected to the solar modules for the energy supply via line pair 220 and hereby obtain the needed energy directly. Further, detection units 210 are connected via an open collector output 215 by means of a single-wire bus 216 to an input 245 of control device 240. The potential of single-wire bus 216 is predefined by control device 240 and is preferably "high." If soiling, which is above the reliable threshold of detection unit 210, is now determined by a detection unit 210, the potential of the bus is clamped to ground for a certain time period. The position of the module, for example, can be easily determined from the time length of the potential clamped to ground. The potential of the bus is monitored by the detection units and then clamped to ground only when another detection unit also does not clamp the potential of the bus to ground.

The invention claimed is:

1. A device for detecting soiling comprising:
   a light source which emits a light beam;
   a layer having a first boundary surface and a second boundary surface,
   a receiver for receiving light scattered from said first and secondary boundary surface wherein the light beam emitted by the light source first impinges on the first boundary surface with a scattered portion of the light beam being scattered at the first boundary surface and received by said receiver as a reference signal and a second portion of the light beam passing through said layer and impinging on said second boundary and another scattered portion of the light beam scattered at said second boundary surface and received by said receiver as a measuring signal; and
   an evaluator for comparing the reference signal and the measuring signal to determine a measure of the soiling of the secondary boundary surface.

2. The device according to claim 1, wherein the surface of the first boundary surface is roughened.

3. The device according to claim 1, wherein a scattering film is arranged on the first boundary surface.

4. The device according to claim 1, wherein the receiver has a first receiving surface and a second receiving surface.

5. The device according to claim 1, wherein the light scattered at the first boundary surface and the light scattered at the second boundary surface substantially impinge on different receiving surfaces.

6. The device according to, claim 1, wherein the optical axis of the light beam is selected so that in the case of a direct reflection of the light beam at the boundary surfaces, the reflected fraction substantially does not impinge on the receiver directly.

7. The device according to claim 1, wherein the receiver has a reference signal output, connected to an inverting input of an operational amplifier, and a measuring signal output, connected to a noninverting input of the operational amplifier.

8. The device according to claim 7, wherein a controllable voltage divider is provided between the inverting input and the reference signal output.

9. The device according to claim 1, wherein a control device for controlling the light source and the voltage divider is provided and the control device has an output for outputting a signal for the extent of soiling.

10. A method for detecting soiling on a layer, which has a first boundary surface and a second boundary surface, the method comprising:
    directing a light beam from a light source unto said first boundary surface;
    directing a scattered portion of light scattered from said first boundary surface onto a receiver to provide a reference signal wherein a potion of light from the beam passes through said layer and impinges on said secondary boundary surface;
    directing another scattered portion of light scattered by said second boundary surface onto said receiver to provide a measuring signal; and
    measuring a soiling of said layer by comparing the reference signal and the measuring signal.

11. The method according to claim 10, wherein substantially only the scattered light fractions of the two boundary surfaces are transmitted to the receiver.

12. The method according to claim 10 wherein soiling is detected when the measuring signal is greater than the reference signal.

13. The method according to claim 10, wherein the comparison of the reference signal with the measuring signal is carried out at time intervals by a control device and the result of the comparison is transmitted wirelessly or hard-wired to a host device.

14. The method according to claim 13, wherein the control device is supplied with the energy of a solar cell and in the event of soiling a signal is provided by the control device by means of an open collector circuit.

15. The device according to claim 1 wherein the soiling is on surfaces of solar collectors and/or solar cells and/or glass panes.

16. The method according to claim 10 wherein the soiling is on surfaces of solar collectors and/or solar cells and/or glass panes.

* * * * *